United States Patent [19]
Schulte et al.

[11] Patent Number: 4,795,437
[45] Date of Patent: Jan. 3, 1989

[54] SIPHON CONTROL DEVICE

[75] Inventors: Rudolf R. Schulte, Santa Barbara; Stephen W. Laguette, Goleta; Gary P. East, Santa Barbara, all of Calif.

[73] Assignee: Pudenz-Schulte Medical Research Corporation, Santa Barbara, Calif.

[21] Appl. No.: 8,650

[22] Filed: Jan. 29, 1987

[51] Int. Cl.$^4$ ............................................. A61M 27/00
[52] U.S. Cl. ...................................... 604/10; 137/510; 604/247
[58] Field of Search ...................................... 604/8–10, 604/185, 247, 93; 137/510

[56] References Cited

U.S. PATENT DOCUMENTS

| | | | |
|---|---|---|---|
| 2,563,665 | 8/1951 | Thomas | 137/53 |
| 2,585,575 | 2/1952 | Nedergaard | 137/53 |
| 2,599,979 | 6/1952 | Drane | 137/53 |
| 2,610,645 | 9/1952 | Wagner | 137/188 |
| 2,704,548 | 3/1955 | Ralston | 137/469 |
| 2,902,048 | 9/1959 | Ryan | 137/510 |
| 3,111,125 | 11/1963 | Schulte | 128/350 |
| 3,469,582 | 9/1969 | Jackson | 128/276 |
| 3,492,996 | 2/1970 | Fountain | 128/350 |
| 3,503,402 | 3/1970 | Schulte | 128/350 |
| 3,595,240 | 7/1971 | Mishler | 128/232 |
| 3,601,128 | 8/1971 | Hakim | 128/350 |
| 3,683,929 | 8/1972 | Holter | 128/350 V |
| 3,756,243 | 9/1973 | Schulte | 128/350 |
| 3,762,681 | 10/1973 | McKinney et al. | 251/61.1 |
| 3,768,508 | 10/1973 | Schulte | 128/350 V |
| 3,769,982 | 11/1973 | Schulte | 128/350 |
| 3,827,439 | 8/1974 | Schulte et al. | 128/274 |
| 3,886,948 | 6/1975 | Hakim | 128/350 V |
| 3,889,687 | 6/1975 | Harris et al. | 128/274 |
| 3,894,541 | 7/1975 | El-Shafei | 128/350 R |
| 3,901,245 | 8/1975 | Spitz et al. | 128/350 V |
| 3,985,140 | 10/1976 | Harris | 128/274 |
| 3,991,768 | 11/1976 | Portnoy | 128/350 V |
| 3,999,553 | 12/1976 | Spitz et al. | 128/350 V |
| 4,332,255 | 6/1982 | Hakim et al. | 128/350 V |
| 4,364,395 | 12/1982 | Redmond et al. | 604/10 |
| 4,464,168 | 8/1984 | Redmond et al. | 604/9 |
| 4,552,553 | 11/1985 | Schulte et al. | 604/9 |
| 4,634,427 | 1/1987 | Hannula et al. | 604/93 |

Primary Examiner—Dalton L. Truluck
Attorney, Agent, or Firm—Kelly, Bauersfeld & Lowry

[57] ABSTRACT

A subcutaneously implantable siphon control device is provided for use in a physiological shunt system including a proximal catheter, a flow control valve and a distal catheter. The siphon control device limits fluid flow through the shunt system due to the siphoning effect of hydrostatic pressure created by the elevation of the proximal catheter inlet with respect to the distal catheter outlet. The siphon control device includes, generally, a base having an inlet typically placed in fluid communication with an outlet of the flow control valve, and an outlet typically placed in fluid communication with the distal catheter, and a housing for the base which, in connection with the base, defines a fluid flow pathway between the inlet and the outlet. The base provides a wall having substantially parallel upper and lower seating surfaces, which separates the inlet from the outlet. A pair of spaced, substantially parallel, flexible and elastic diaphragms having inner and outer surfaces are provided by the housing, and are situated on opposite sides of the wall to position a portion of each inner surface in contact with an adjacent one of the seating surfaces.

17 Claims, 2 Drawing Sheets

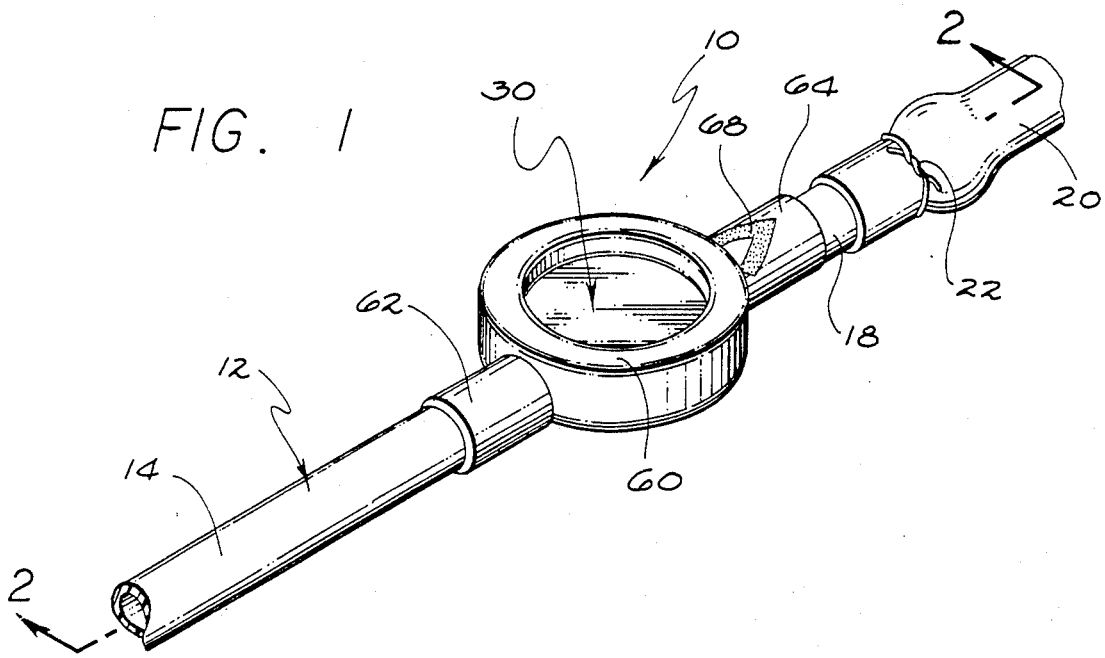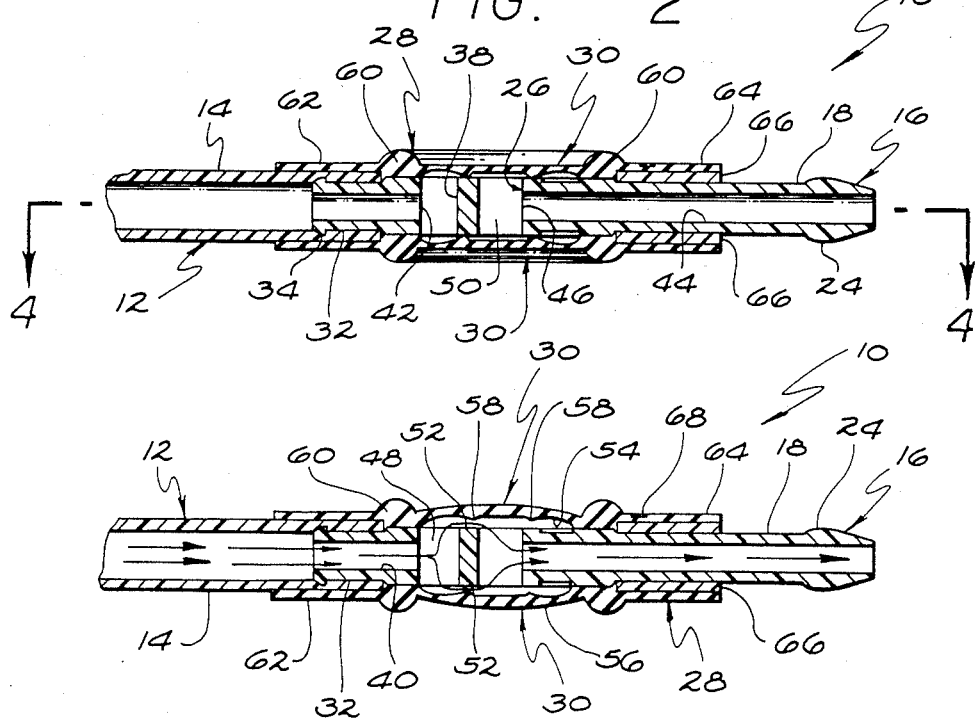

SIPHON CONTROL DEVICE

BACKGROUND OF THE INVENTION

This invention relates generally to physiological drainage systems, and, more specifically, to a siphon control device for limiting fluid flow through such systems due to the siphoning effect of hydrostatic pressure.

In the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in which fluids accumulate within the skull and exert extreme pressure and skull deforming forces.

In treating hydrocephalus, cerebrospinal fluid accumulated in the brain ventricles is typically drained away utilizing a drainage or shunt system including a catheter inserted into the ventricle through the skull, which is connected to a tube which conducts the fluid away from the brain to be reintroduced into the peritoneal cavity or into the vascular system, as by extending a distal catheter through the patent's jugular vein to the atrium portion of the heart. To control the flow of cerebrospinal fluid and maintain the proper pressure in the brain ventricle, a pump or valve is placed in the conduit between the brain and the peritoneal cavity or the heart. Exemplary valves are found in U.S. Pat. Nos. 4,552,553 and 4,560,375, the contents of which are incorporated by reference herein.

Although such drainage systems have provided successful results, a problem of overdrainage of the cerebrospinal fluid from the brain ventricles sometimes exists. Overdrainage of cerebrospinal fluid may result in excessive reduction of the cerebrospinal fluid pressure within the brain ventricles and predispose the development of a subdural hematoma or hydroma, and excessive reduction of ventricular size leading to shunt obstruction because of impingement of the ventricular walls on the inlet holes of the ventricular cathether. This overdrainage can be caused by the siphoning effect of hydrostatic pressure in the distal shunt catheter. The siphoning effect of hydrostatic pressure may be created by the elevation of the ventricular catheter inlet with respect to the distal catheter outlet (i.e., when the patient sits, stands or is held erect).

Accordingly, there has been a need for a novel subcutaneously implantable siphon control device for use in a physiological shunt system which can effectively prevent overdrainage of fluid through the system due to the siphoning effect of hydrostatic pressure. It would be preferable that such a novel siphon control device be normally closed, open only in response to positive upstream fluid pressure, and re-close or remain closed in the absence of such positive upstream fluid pressure or in response to negative downstream hydrostatic pressure. Further, a siphon control device is needed which utilizes dissimilar materials to inhibit component sticking and deformation, and which includes integral connectors. Moreover, a siphon control device is needed which has an uncomplicated internal flow path and design which eliminates anterior/posterior positioning concerns. The present invention fulfills these needs and provides other related advantages.

SUMMARY OF THE INVENTION

The present invention resides in an improved physiological siphon control device capable of effectively limiting drainage of fluid through a shunt or drainage system under hydrostatic/siphoning conditions. The siphon control device comprises, generally, a base having an inlet and an outlet, and a housing for the base which, in connection with the base, defines a fluid flow pathway between the inlet and the outlet. An inner wall separates the inlet from the outlet, and interacts with a diaphragm means overlying the base to form a seal therebetween. This seal prevents fluid flow between the inlet and the outlet except under defined conditions to prevent excessive drainage due to downstream siphoning.

In a preferred form of the invention, the outlet includes an outlet connector having an outlet port at its proximal end. An outlet chamber is provided adjacent to and in fluid communication with the outlet port. This outlet chamber is defined, in part, by the inner wall which extends continuously from one side of the outlet port to the opposite side of the outlet port. This inner wall further has substantially parallel upper and lower seating surfaces which interact with the diaphragm means.

The inlet includes an inlet connector having an inlet port at its distal end. A central reservoir is provided adjacent to and in fluid communication with the inlet port. The central reservoir is separated from the outlet chamber by the inner wall, and is further defined, at least in part, by an outer wall spaced from the inner wall and extending from the inlet connector to the outlet connector. In this manner, the central reservoir substantially encircles the outlet chamber.

The diaphragm means forms a portion of the housing in which the base is situated, and includes a pair of spaced, substantially parallel, flexible and elastic diaphragms fixed about their peripheries adjacent the outer wall. Each diaphragm has an inner surface defining portions of the outlet chamber and the central reservoir, and an outer surface forming an exterior surface of the siphon control device. The diaphragms are situated on opposite sides of the inner wall to position a portion of each inner surface in contact with an adjacent one of the seating surfaces and form a seal therebetween which prevents fluid flow between the inlet and the outlet. In this regard, the portion of each inner surface contacting the adjacent one of the seating surfaces includes a seating ridge extending inwardly from the respective diaphragm.

This construction and positioning of the diaphragms with respect to the inner wall permits movement of the diaphragms away from the seating surfaces in response to positive fluid pressure within the central reservoir to allow passage of fluid from the inlet to the outlet through the device. The seating ridges of the diaphragms will engage the adjacent seating surfaces of the inner wall to form a seal which prevents such fluid flow, however, in the absence of such positive fluid pressure or in response to hydrostatic pressure in the outlet chamber.

Means for inhibiting the tissue overlying the diaphragms from occluding the device are provided, and include an offset ring surrounding each diaphragm. The housing is preferably formed of a silicone elastomer material, and the base is preferably formed of a relatively rigid plastic material. This combination of materials is intended to prevent sticking between the sealing surfaces of the diaphragms and the inner wall. The housing further preferably includes a tantalum directional marker, and radiopaque indicator means are provided which encircle portions of the inlet connector and the outlet connector. Moreover, the inlet can include a section of inlet tubing fixed at its distal end to the base, which inlet tubing, in connection with the inlet connector, channels fluid to the inlet port.

In another preferred form of the invention, all elements of the siphon control device are as described above with the exception that the seating ridge extending inwardly from each respective diaphragm is omitted. The fact that the seating ridges may be omitted illustrates that various configurations may be used to create the necessary seal between the diaphragms and the inner wall to prevent fluid flow from the inlet to the outlet.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a preferred form of the siphon control device of the present invention, shown connected to surgical tubing at its distal end;

FIG. 2 is an elevational, sectional view of the siphon control device of the present invention, taken substantially along the line 2—2 of FIG. 1;

FIG. 3 is an elevational, sectional view similar to that illustrated in FIG. 2, further showing the manner in which a pair of diaphragms move outwardly from an inner wall in response to positive fluid pressure within an inlet, to permit fluid flow from the inlet to the outlet;

DETAILED DESCRIPTION OF THE PREFERRED EMBODIMENTS

Figure 4:
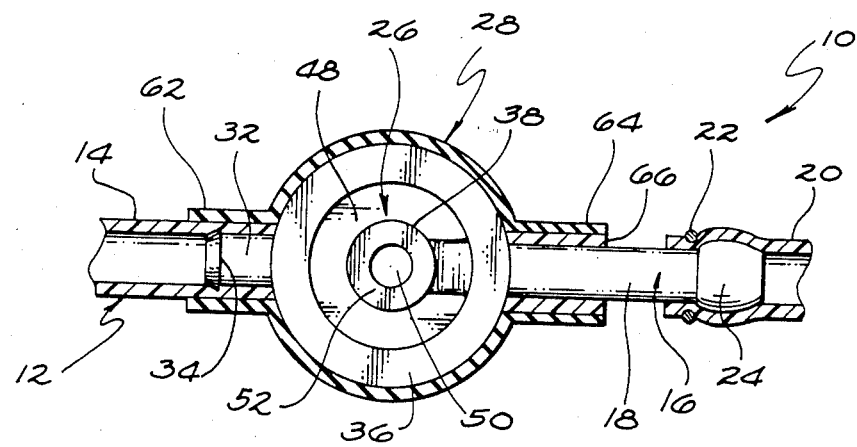
FIG. 4 is a top plan, sectional view of the siphon control device of the present invention, taken substantially along the line 4—4 of FIG. 2.

As shown in the drawings for purposes of illustration, the present invention is concerned with an improved siphon control device, generally designated in the accompanying drawings by the reference number 10. The siphon control device 10 of the present invention is intended primarily for use in surgically implanted systems for draining fluid from one portion of the human body to another, to prevent excessive drainage which may be caused by the siphoning effect of hydrostatic pressure in a distal shunt catheter (not shown).

In order to connect the siphon control device 10 in such a system, it is provided an inlet 12 including a section of inlet tubing 14, and an outlet 16 including an outlet connector 18. The outlet connector 18 is configured to receive one end of a piece of surgical tubing 20 which is slid over the connector and typically secured by a single ligature 22. The ligature 22 is preferably secured around the tubing 20 just inside an annular ridge 24 formed near the end of the outlet connector 18. The inlet tubing 14, on the other hand, is configured to be received onto an outlet connector for a suitable flow control valve, such as any one of those illustrated in U.S. Pat. Nos. 4,560,375 and 4,636,194, and secured in the same manner as the tubing 20 discussed above.

In accordance with the present invention, and as illustrated with respect to a first embodiment in FIGS. 1 through 4, the siphon control device 10 includes a molded polypropylene base 26 invested in a smooth, flexible silicone elastomer casing or housing 28 having two integral flexible diaphragms 30. The polypropylene base 26 contributes to the structural integrity of the device 10 and inhibits possible distortion and sticking of the flexible silicone elastomer diaphragms 30.

The base 26 includes an inlet connector 32 having an annular ridge 34 for securing the inlet tubing 14 thereto, an outer wall 36, an inner wall 38 situated within and encircled by the outer wall, and the outlet connector 18. The inlet connector 32 provides a tubular passageway 40 for channeling fluids received from the inlet tubing 14 to an inlet port 42 situated through the outer wall 36. The outlet connector 18, on the other hand, provides a separate tubular passageway 44 from an outlet port 46 to the distal end of the outlet connector 18.

As can be seen best in FIG. 4, the outer wall 36 is generally circular in shape, and is spaced from and encircles the inner wall 38. The area between the inner wall 38 and the outer wall 36 comprises a central reservoir 48 which is adjacent to and in fluid communication with the inlet port 42. The inner wall 38 is also generally circular in shape, and defines an outlet chamber 50 which is adjacent to and in fluid communication with the outlet port 46. The inner wall 38 is constructed to have substantially parallel upper and lower seating surfaces 52, and it effectively forms a barrier separating the central reservoir 48 from the outlet chamber 50.

The pair of spaced, substantially parallel, flexible and elastic diaphragms 30 are fixed about their peripheries adjacent the outer wall 36. Each diaphragm has an inner surface 54 which defines the upper and lower limits of the central reservoir 48 and the outlet chamber 50, and an outer surface 56 which forms an exterior surface of the siphon control device 10. The diaphragms 30 are situated on opposite sides of the inner wall 38 to position a portion of each inner surface 54 in contact with an adjacent one of the seating surfaces 52 and form a seal therebetween which prevents fluid flow between the inlet 12 and the outlet 16. To help facilitate the formation of this seal, a seating ridge 58 is integrally molded onto the inner surface 54 of each diaphragm 30 to extend inwardly therefrom and contiguously meet and seal with the adjacent seating surface 52.

The housing 28 further includes an integral offset ring 60 which surrounds each diaphragm 30 to inhibit the overlying tissue from occluding the device 10 when implanted into a patient. Extending both distally and proximally from the offset rings 60 are sealing flanges 62 and 64 which encircle, respectively, portions of the inlet connector 32 and the oulet connector 18. The distal end of the inlet tubing 14 is positioned between the sealing flange 62 and the inlet connector 32, and a seal is effected between these components to prevent fluid leakage between the base 26 and the housing 28. Similarly, a silicone seal tube 66 is placed between the sealing flange 64 and the adjacent portion of the outlet connector 18 to form a fluid tight seal between the base 26 and housing 28.

It is preferred that the inlet tubing 14 be constructed of a barium inpregnated silicone elastomer material to permit x-ray detection of the location of that tubing. The seal tube 66 is likewise also preferably constructed of a radiopaque barium silicone material to facilitate the percutaneous detection of separation of the surgical tubing 20 from the outlet connector 18. Embedded within the top of the sealing flange 64 is a tantalum directional marker in the form of an arrow 68. This is placed on the device 10 to facilitate proper orientation of the device by the surgeon.

In use, the diaphragms 30 will normally lie against and interact with the seating surfaces 52 of the inner wall 38 to close the device 10 to fluid flow from the inlet 12 to the outlet 16. The diaphragms 30 will move away from the seating surfaces 52, however, in response to a minimal level of positive fluid pressure within the central reservoir 48 to permit passage of fluid from the inlet 12 to the outlet 16 through the device 10 (see FIG. 3). The diaphragms 30 will close and seal upon the seating surfaces 52 once again in the absence of such positive upstreamf fluid pressure, or in response to negative downstream hydrostatic pressure in the outlet chamber 50. The siphon control device 10 of the present invention thus minimizes the undesirable consequences attendant to excessive overdrainage of fluid due to the siphoning effect of hydrostatic pressure.

Figure 5:
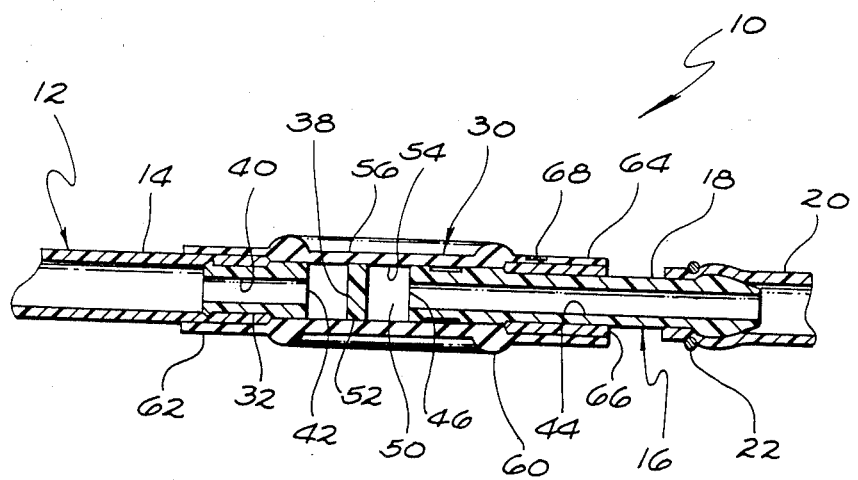
FIG. 5 is an elevational, sectional view of an alternative embodiment of the siphon control device of the present invention, taken substantially along the line 2—2 of FIG. 1, illustrating the use of flexible diaphragms having flat inner surfaces which do not utilize the seating ridges found in the primary embodiment of FIGS. 1 through 4.

With reference to FIG. 5, an alternative embodiment of the siphon control device 10 of the present invention as shown. The only difference between the embodiment shown in FIG. 5 with that shown in FIGS. 1 through 4 is the absence of the seating ridges 58 on the inner surfaces 54 of the diaphragms 30. In this alternative embodiment, the diaphragms 30 are situated to lie substantially flat against the seating surfaces 52 of the inner wall 38. The diaphragms 30 function in an identical manner as described above to effectively limit fluid flow through an associated physiological shunt system due to the siphoning effect of hydrostatic pressure created by the elevation of a proximal catheter inlet (not shown) with respect to a distal catheter outlet (also not shown).

From the foregoing, it should be apparent that the siphon control device 10 of the present invention provides a normally closed device for inhibiting excessive drainage through a physiological shunt in the presence of excessive downstream suction. The siphon control device 10 of the present invention opens only in response to positive upstream fluid pressure, and then only in the absence of negative downstream hydrostatic pressure. The design of the siphon control device 10 eliminates anterior/posterior positioning concerns due to the provision of oppositely situated diaphragms 30, and provides a simple, uncomplicated internal flow path through the device. There is no metal which could possibly interfere with CAT Scan or NMR imagery, however, the barium impregnated inlet tubing 14 and the radiopaque seal tube 66 facilitate percutaneous examination of the device 10. Finally, dissimilar materials (polypropylene and flexible silicone elastomer components) inhibit diaphragm sticking and deformation.

Alhough two particular embodiments of the invention have described in detail for purposes of illustration, various modifications of each may be made without departing from the spirit scope of the invention. Accordingly, the invention is not to be limited, except as by the appended claims.

We claim:

1. A siphon control device for use in a physiological shunt system, comprising:
    a base including an inlet, an outlet, an inner wall which separates the inlet from the outlet, and an outer wall spaced from the inner wall and extending from the inlet to the outlet, wherein the inner wall has substantially parallel upper and lower seating surfaces;
    a housing for the base which, in connection with the base, defines a fluid flow pathway between the inlet and the outlet, the housing including diaphragm means fixed about its periphery adjacent the outer wall, wherein the diaphragm means includes a pair of spaced, substantially parallel, flexible diaphragms situated on opposite sides of the wall to position a portion of each diaphragm such that said portion is normally in contact with an adjacent one of the seating surfaces, each diaphragm having an outer surface forming an exterior surface of the siphon control device, and an inner surface having a portion positioned adjacent an edge of the inner wall to normally form a seal therebetween which prevents fluid flow between the inlet and the outlet, wherein at least one of the inner surfaces will move away from the adjacent edge of the inner wall in response to positive fluid pressure within the inlet to permit passage of fluid from the inlet to the outlet, but will form a seal with the inner wall to prevent such fluid flow in response to negative hydrostatic pressure in the outlet; and
    means for inhibiting tissue overlying the diaphragm means for occluding the device, wherein the inhibiting means includes top and bottom offset rings, each of which surrounds a respective diaphragm by extending outwardly from the device to form a recess in which a diaphragm is positioned.

2. A siphon control device as set forth in claim 1, wherein the inhibiting means is integrally formed with the housing, and includes an offset ring surrounding each diaphragm.

3. A siphon control device as set forth in claim 1, including an outlet chamber defined, in part, as the space between the inner wall and the outlet port, and a central reservoir defined, in part, as the space between the inner wall and outer wall, wherein the central reservoir substantially encircles the outlet chamber.

4. A siphon control device as set forth in claim 1, wherein the portion of the inner surface positioned adjacent the edge of the inner wall to form a seal therebetween includes a seating ridge extending inwardly toward the adjacent edge of the inner wall.

5. A subcutaneously implantable siphon control device, comprising:
    an integral housing including a pair of spaced, substantially parallel, flexible diaphragms having inner and outer surfaces, and top and bottom integral rings wherein each is positioned to surround a respective diaphragm to provide means for inhibiting overlying tissue from occluding the device; and
    a base invested within the housing, the base including an inlet, an outlet and a wall which separates the inlet from the outlet, the wall having substantially parallel upper and lower seating surfaces;
    wherein the base and housing define a fluid flow pathway between the inlet and the outlet, the diaphragms being situated on opposite sides of the wall to position a portion of each inner surface to be normally in contact with an adjacent one of the seating surfaces and form a seal therebetween which prevents fluid flow between the inlet and the outlet, wherein the diaphragms will move away from the seating surfaces in response to positive fluid pressure on the inlet side of the wall to permit passage of fluid from the inlet to the outlet through the device, but will form a seal with the seating surfaces to prevent such fluid flow in the absence of such positive fluid pressure or in response to negative hydrostatic pressure on the outlet side of the wall.

6. A siphon control device as set forth in claim 5, wherein the inlet includes an inlet connector having an inlet port at its distal end, and wherein the outlet includes an outlet connector having an outlet port at its proximal end.

7. A siphon control device as set forth in claim 6, including an outlet chamber defined by the wall, the outlet port and by portions of the diaphragms, a central reservoir in fluid communication with the inlet port and separated from the outlet chamber by the wall, wherein the central reservoir is defined, in part, by an outer wall spaced from the wall and extending from the inlet connector to the outlet connector.

8. A siphon control device as set forth in claim 6, including radiopaque indicator means encircling portions of the inlet connector and the outlet connector.

9. A siphon control device as set forth in claim 6, wherein the inlet includes a section of inlet tubing attached to the inlet connector which, with the inlet connector, channels fluid to the inlet port.

10. A siphon control device as set forth in claim 5, wherein the portion of each inner surface contacting the adjacent one of the seating surfaces includes a seating ridge extending inwardly from the respective diaphragm.

11. A siphon control device as set forth in claim 1, wherein the inhibiting means is integrally formed with the housing, and extends outwardly from the device to form a recess in which the diaphragms are positioned.

12. A subcutaneously implantable siphon control device for use in a physiological shunt system, comprising:

a base including an inlet, an outlet, and an inner wall which separates the inlet from the outlet, the inner wall having substantially parallel upper and lower planar seating surfaces and an outer wall spaced from the inner wall and extending from the inlet to the outlet. wherein the inner and outer walls cooperatively define, at least in part, an outlet chamber adjacent to and in fluid communication with the outlet, and a central reservoir adjacent to and in fluid communication with the inlet, wherein the central reservoir and the outlet chamber are concentric chambers with the central reservoir being separated from the outlet chamber by the inner wall;

a housing for the base which, in connection with the base, defines a fluid flow pathway between the inlet and the outlet whereby fluid flow is split by the inner wall into first and second flow streams which flow around the entire upper and lower seating surfaces respectively, the housing including diaphragm means fixed about the base, wherein the diaphragm means includes a pair of spaced, substantially parallel, flexible diaphragms situated on opposite sides of the inner wall to position a portion of each diaphragm to be normally in contact with an adjacent one of the planar seating surfaces, each diaphragm having an outer surface forming an exterior surface of the siphon control device, and an inner surface having a portion positioned adjacent to a seating surface of the inner wall to normally form a seal therebetween which prevents fluid flow between the inlet and the outlet, said portion of each inner surface including a seating ridge which extends inwardly from the respective diaphragm, wherein the concentric chambers are closed only upon flexing of both diaphragms, and wherein at least one of the inner surfaces will move away from the adjacent edge of the inner wall in response to positive fluid pressure within the inlet to permit passage of fluid from the inlet to the outlet, but will form a seal with the inner wall to prevent such fluid flow in response to negative hydrostatic pressure in the outlet; and means for inhibiting tissue overlying the diaphragm means from occluding the device, wherein the inhibiting means includes top and bottom offset rings, each of which surrounds a respective diaphragm, each ring being integrally formed with the housing and extending outwardly from the device to form a recess in which a diaphragm is positioned.

13. A siphon control device as set forth in claim 12, wherein the inlet includes an inlet connector having an inlet port at its distal end, and wherein the outlet includes an outlet connector having an outlet port at its proximal end.

14. A siphon control device as set forth in claim 12, wherein the housing is formed of an elastomeric material, and the base is formed of a relatively rigid material.

15. A siphon control device as set forth in claim 13, including radiopaque markers encircling portions of the inlet connector and the outlet connector.

16. A siphon control device as set forth in claim 15, wherein the housing includes a directional marker for facilitating proper orientation of the device.

17. A siphon control device as set forth in claim 13, wherein the inlet includes a section of inlet tubing attached to the inlet connector which, with the inlet connector, channels fluid to the inlet port.

* * * * *